United States Patent
Lu et al.

(10) Patent No.: US 9,275,194 B2
(45) Date of Patent: Mar. 1, 2016

(54) SYSTEM AND METHOD OF MULTI-USER COACHING INSIDE A TUNABLE MOTION-SENSING RANGE

(71) Applicant: Industrial Technology Research Institute, Hsinchu (TW)

(72) Inventors: Tung-Hung Lu, Yilan County (TW); Hsing-Chen Lin, Taichung (TW); Yueh-Hsuan Lee, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 208 days.

(21) Appl. No.: 14/249,361

(22) Filed: Apr. 10, 2014

(65) Prior Publication Data

US 2015/0098625 A1    Apr. 9, 2015

(30) Foreign Application Priority Data

Oct. 4, 2013   (TW) .............................. 102136045 A

(51) Int. Cl.
   *G06K 9/00*     (2006.01)
   *G06F 19/00*    (2011.01)
(52) U.S. Cl.
   CPC .................................. *G06F 19/3481* (2013.01)
(58) Field of Classification Search
   None
   See application file for complete search history.

(56) References Cited

U.S. PATENT DOCUMENTS

| | | | |
|---|---|---|---|
| 7,961,174 B1 | 6/2011 | Markovic et al. | |
| 2010/0195867 A1* | 8/2010 | Kipman | A63F 13/10 382/103 |
| 2010/0277411 A1 | 11/2010 | Yee et al. | |
| 2010/0306685 A1* | 12/2010 | Giaimo, III | A63F 13/10 715/765 |
| 2010/0306712 A1* | 12/2010 | Snook | G06K 9/00342 715/863 |
| 2010/0306714 A1* | 12/2010 | Latta | G60F 3/017 715/863 |
| 2011/0035666 A1* | 2/2011 | Geisner | G06F 3/011 715/709 |
| 2011/0175809 A1 | 7/2011 | Markovic et al. | |
| 2011/0228976 A1* | 9/2011 | Fitzgibbon | G06K 9/00335 382/103 |

(Continued)

FOREIGN PATENT DOCUMENTS

| | | |
|---|---|---|
| CN | 102221886 | 10/2011 |
| TW | I286717 | 9/2007 |

(Continued)

OTHER PUBLICATIONS

"Office Action of Taiwan Counterpart Application", issued on Nov. 3, 2015, p. 1-p. 9, in which the listed reference was cited.

(Continued)

*Primary Examiner* — Sean Motsinger
(74) *Attorney, Agent, or Firm* — Jianq Chyun IP Office

(57) ABSTRACT

A system and a method of multi-user coaching are introduced herein. Motion-sensing cameras are applied to capture images, and a depth image stitching module is applied to perform a depth image stitching process on the captured images to expand the motion-sensing range, so as to establish a virtual environment for multi-user coaching. Each user can be coached individually by a one-to-multiple approach to improve his or her motions. By using the system and the method of multi-user coaching, that is, the system can only calculates on motion similarities of the users, and instructions are fed back to each user. Therefore, the system and the method described herein can be extensively applied to various products, such as a virtual gymnasium, a virtual aerobics classroom, a virtual Budokan, and so on.

18 Claims, 7 Drawing Sheets

(56) References Cited

U.S. PATENT DOCUMENTS

| | | | | |
|---|---|---|---|---|
| 2011/0304632 | A1* | 12/2011 | Evertt | G06F 3/011 345/474 |
| 2011/0306396 | A1* | 12/2011 | Flury | A63F 13/10 463/7 |
| 2011/0316963 | A1* | 12/2011 | Li | H04N 7/15 348/14.1 |
| 2012/0113092 | A1* | 5/2012 | Bar-Zeev | G02B 27/017 345/419 |
| 2012/0190505 | A1* | 7/2012 | Shavit | A63B 71/0622 482/8 |
| 2012/0293518 | A1* | 11/2012 | Geisner | G06F 3/011 345/474 |
| 2013/0034264 | A1* | 2/2013 | Lin | G06K 9/00342 382/103 |
| 2013/0083064 | A1* | 4/2013 | Geisner | G06F 17/30047 345/633 |
| 2013/0286004 | A1* | 10/2013 | McCulloch | G06T 19/006 345/419 |
| 2014/0073383 | A1* | 3/2014 | Lu | A63F 13/04 463/7 |
| 2014/0147820 | A1* | 5/2014 | Snow | G06F 19/3481 434/247 |

FOREIGN PATENT DOCUMENTS

| | | |
|---|---|---|
| TW | 201111014 | 4/2011 |
| TW | 201242641 | 11/2012 |
| TW | 201308253 | 2/2013 |

OTHER PUBLICATIONS

Albaina et al., "Flowie: A Persuasive Virtual Coach to Motivate Elderly Individuals to Walk," PervasiveHealth 2009 3rd International Conference on Pervasive Computing Technologies for Healthcare, Apr. 1-3, 2009, pp. 1-7.

Tim Wortmann, "Automatic Stitching of Micrographs using Local Features," 2010 International Symposium on Optomechatronic Technologies (ISOT), Oct. 25-27, 2010, pp. 1-6.

Lu et al., "A Motion-Sensing Enabled Personalized Exercise System for Cardiac Rehabilitation," 2012 IEEE 14th International Conference on e-Health Networking, Applications and Services (Healthcom), Oct. 10-13, 2012, pp. 167-171.

Faion et al, "Intelligent Sensor-Scheduling for Multi-Kinect-Tracking," 2012 IEEE/RSJ International Conference on Intelligent Robots and Systems (IROS), Oct. 7-12, 2012, pp. 3993-3999.

Lou et al., "A Multi-User Interaction System Based on Kinect and Wii Remote," 2012 IEEE International Conference on Multimedia and Expo Workshops (ICMEW), Jul. 9-13, 2012, pp. 667.

* cited by examiner

SYSTEM AND METHOD OF MULTI-USER COACHING INSIDE A TUNABLE MOTION-SENSING RANGE

CROSS-REFERENCE TO RELATED APPLICATION

This application claims the priority benefit of Taiwan application serial no. 102136045, filed on Oct. 4, 2013. The entirety of the above-mentioned patent application is hereby incorporated by reference herein and made a part of this specification.

TECHNICAL FIELD

The disclosure relates to a system and a method of multi-user coaching inside a tunable motion-sensing range.

BACKGROUND

Nowadays, people pay more attention to proper physical exercise. In recent years, the diversity of sports allow people not to work out on the equipment in general fitness gyms but also to do exercise for full-body fitness, such as dancing, aerobics, rhythmic gymnastics, etc. Thereby, people do not get bored and are able to persevere in exercising.

Most of the full-body exercises should be paid for requiring the coach at the fitness gym. However, the coach cannot well instruct individual users due to numerous students at the gym, the students neither learn effectively nor fully understand the correct posture.

When a player plays the commercial games via the Kinect on XBOX360 KINECT, his or her movement can be tracked by the KINECT sensor to experience the most real sport amusement by undergoing the professional one-by-one fitness program in a friendly virtual gym. However, the virtual private coach only guide one player in a one-by-one program to compare his or her similarity scores at certain time frames, and it also cannot compare similarity scores with multiple players through consecutive time frames nor evaluate the correctness of the posture or the motion of individual player. In addition, the view-angle range of the infrared Kinect sensor in the horizontal direction is only 57.5°, which will limit the detection range of the research, development, and even application. Moreover, to provide images with the expanding range, the image stitching technique is only applied to stitch images by multiple RGB cameras.

SUMMARY

The disclosure provides a multi-user coaching system, and the system includes an image processing unit, a user motion capturing unit, a multithreading processing unit, a multi-user comparing unit, and a coaching database. The image processing unit receives a plurality of images in parallel and performs a depth image stitching process and a user skeleton capturing process on the plurality of images to obtain a plurality of user information. The user motion capturing unit generates a plurality of depth streaming motion images and a plurality of node information corresponding to each of the plurality of user information. The multithreading processing unit transmits in parallel the node information and the plurality of depth streaming motion images corresponding to the plurality of user information. The multi-user comparing unit is coupled to the multithreading processing unit, and receives and compares the plurality of depth streaming motion images and the node information with virtual coach information to generate a plurality of personalized comparing results. The coaching database stores a plurality of predetermined motion instructions and outputs the motion instructions corresponding to the personalized comparing results.

The disclosure provides a multi-user coaching method. In the method, a plurality of images is received in parallel, and a depth image stitching process and a user skeleton capturing process are performed on the plurality of images to obtain a plurality of user information. A plurality of depth streaming motion images and a plurality of node information are generated corresponding to each of the user information. The plurality of depth streaming motion images and each of the plurality of node information are comprated with virtual coach information to generate a plurality of personalized comparing results. A plurality of motion instructions are output corresponding to the personalized compared results.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

The existing motion-sensing system can merely be used by one user at one time; that is, the system can only perform calculations on motion similarity of one user, and trigger the motion instruction feedback function for that user, which may be exemplified by the U.S. patent application Ser. No. 13/849, 535 (corresponding to Taiwan patent application No. 101147275 and the P.R. China patent application No. 201210568013.X) proposed by the inventors of this application and entitled "METHOD AND SYSTEM FOR MOTION COMPARISON". The entirety of each of the above-mentioned patent applications is incorporated by reference herein and made a part of this specification. The disclosure is derived from said applications. According to an exemplary embodiment of the disclosure, skeletons of multiple users are input to the system, and the system performs calculations on motion similarity of each user and triggers the motion instruction feedback function for each user. Thereby, the multi-user coaching technology may be applied on various scenarios.

By using the system and the method of multi-user coaching inside a large tunable motion-sensing range, motions of users are compared at the same time to perform calculations on motion similarities and to trigger the motion instruction feedback function for individual user. Thereby, the system and the method described herein may be extensively applied to various scenario and product development, such as a virtual gymnasium, a virtual aerobics classroom, a virtual Budokan, and so on.

In an exemplary embodiment of the disclosure, a multi-user coaching system inside a tunable motion-sensing range is provided. A plurality of motion-sensing cameras are applied to capture images, and a depth image stitching module is applied to perform a depth image stitching process on the captured images to expand the motion-sensing range; thereby, a virtual environment for multi-user coaching is established, and each user can be coached individually by a one-to-multiple approach to improve his or her motions.

Figure 1:
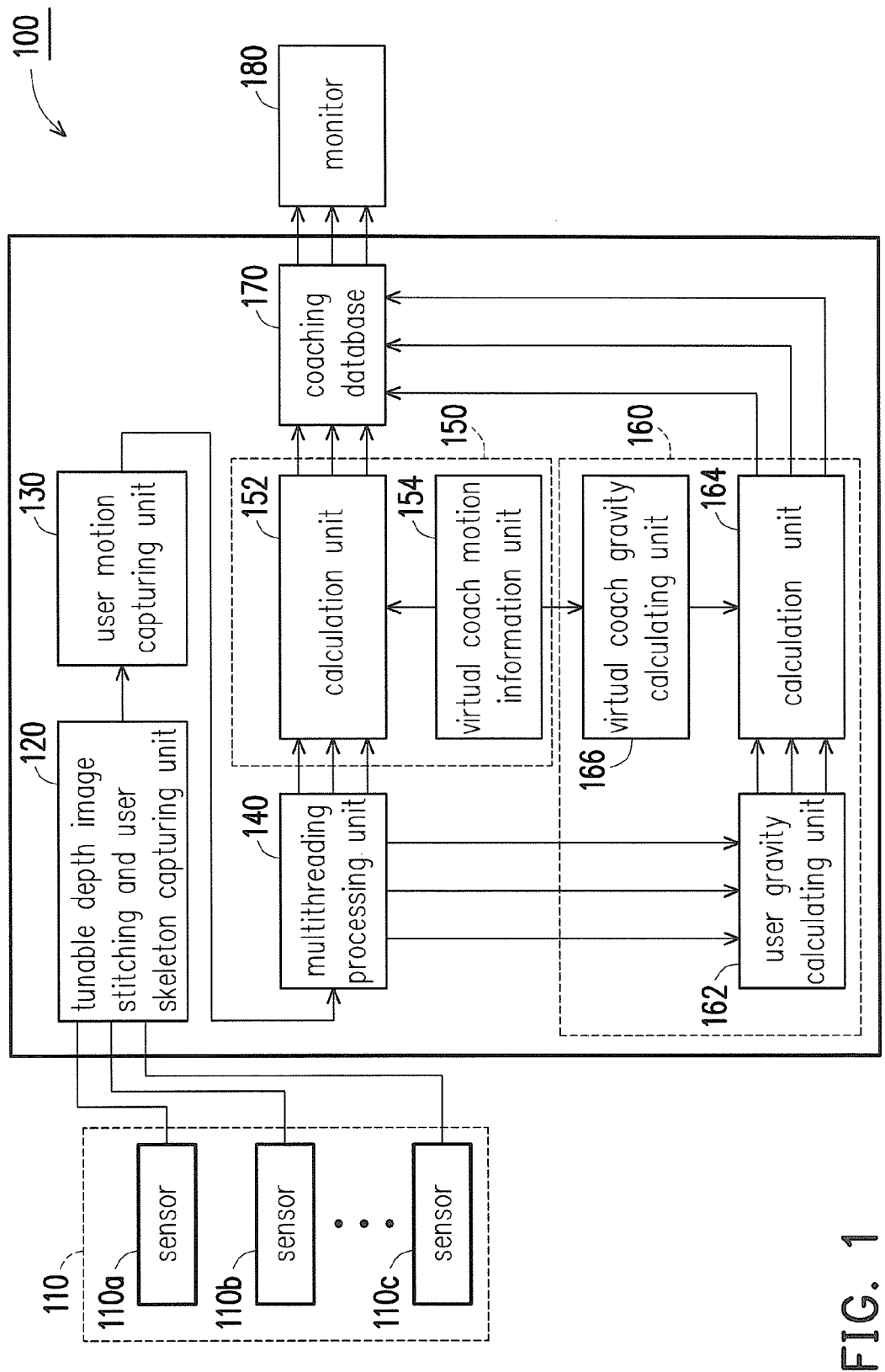
FIG. 1 is a schematic block diagram illustrating a multi-user coaching system inside a tunable motion-sensing range according to one of several exemplary embodiments of the disclosure.

FIG. 1 is a schematic block diagram illustrating a multi-user coaching system inside a tunable motion-sensing range according to one of several exemplary embodiments of the disclosure. Please refer to FIG. 1. The multi-user coaching system 100 inside a tunable motion-sensing range includes an image processing unit (e.g., a tunable depth image stitching and user skeleton capturing unit 120 in FIG. 1), a user motion capturing unit 130, a multithreading processing unit 140, a multi-user motion comparing unit 150, a multi-user gravity comparing unit 160, and a coaching database 170. The multi-user coaching system 100 may include a sensor set 110 or use an existing sensor set provided by an external device 110. The output of the multi-user coaching system 100 is transmitted to a monitor 180 that displays relative information. Each unit of the multi-user coaching system 100 will be explained in the following exemplary embodiments.

The sensor set 110 detects and obtains a plurality of images. The images at least include a plurality of user's images. As shown in FIG. 1, the sensor set 110 includes a plurality of sensors, for example, sensors 110a-110c. However, the disclosure is not limited thereto. Additionally, the sensors in the sensor set 110 can be arranged according to the actual environment requirements. The tunable depth image stitching and user skeleton capturing unit 120 receives the images from the sensors in the sensor set 110, performs stitching calculations on the received images, and obtains the user information in the stitched image. The user information described in the present exemplary embodiment includes the depth information of the images and the information of skeleton nodes. The user motion capturing unit 130 captures a plurality of depth streaming motion images of the users and a plurality of node information from the stitched image.

The depth streaming motion images and the node information of the users are transmitted to the multithreading processing unit 140 to process a plurality of threads in parallel at the same time. Multithreading is a kind of technology of executing the threads in parallel by means of software or hardware. The hardware support of the processor capable of performing the multithreading process allows the processor to execute more than one thread at the same time, and the overall processing performance is enhanced. The system possessing such capability includes a symmetric multiprocessor, a multi-core processor, a chip-level multithreading processor, and a simultaneous multithreading processor. As to software multithreading, even the processor merely executes one thread, the operation system is able to switch between different threads quickly. The time duration at which the operation system switches between different threads is so small as if the multiple threads are executed at the same time, which is referred to as the software multithreading.

The multithreading processing unit 140 respectively transmits the depth streaming motion images and the node information corresponding to the user information to the multi-user motion comparing unit 150 and the multi-user gravity comparing unit 160. In an exemplary embodiment, the multi-user motion comparing unit 150 includes a calculation unit 152 and a virtual coach motion information unit 154. The multi-user gravity comparing unit 160 includes a user gravity calculating unit 162, a calculation unit 164, and a virtual coach gravity calculating unit 166.

In the multi-user motion comparing unit 150, the virtual coach motion information unit 154 provides the pre-recorded virtual coach depth streaming motion images and the node information. The virtual coach motion information unit 154 can process the corresponding information according to the course or the program selected by the user. The calculation unit 152 compares and analyzes the trajectories of a plurality of user depth streaming motion images and the trajectory of the virtual coach depth streaming motion image to provide a plurality of personalized comparing results. For example, there are M users, and then the calculation unit 152 compares and analyzes the trajectories of the M users' depth streaming motion images and the trajectory of the corresponding virtual coach depth streaming motion image.

In the multi-user gravity comparing unit 160, the virtual coach gravity calculating unit 162 which is connected to the virtual coach motion information unit 154 calculates the gravity of the virtual coach depth streaming image. The user gravity calculating unit 162 calculates the gravity of the depth streaming motion images of multiple users at the same time, respectively. The calculation unit 164 compares and analyzes the individual users' gravity shifting trajectories and the virtual coach gravity shifting trajectory at the same time to provide the corresponding personalized gravity shifting comparing and analyzing results.

The coaching database 170 stores advices of the predetermined motion instructions, e.g., the speed of the motion, the location where the motion takes places, the speed and the direction of shifting the gravity, etc. The coaching database 170 searches and outputs appropriate advices of the motion instructions according to the personalized comparing results and the personalized gravity shifting comparing results. The output of the multi-user coaching system 100 inside a tunable motion-sensing range is transmitted to the monitor 180 to display relative information. The monitor 180 displays a plurality of advices of the personalized motion instructions for the users to correct the motions.

By means of the multi-user coaching system inside a tunable motion-sensing range as shown in FIG. 1, motion-sensing cameras are applied to capture depth images, so that a depth image stitching module is applied to perform a depth image stitching process on the captured depth images to expand the motion-sensing range; thereby, a virtual multi-user coaching environment is established. Each user can be coached individually by a one-to-multiple approach to improve his or her motions.

Figure 2:
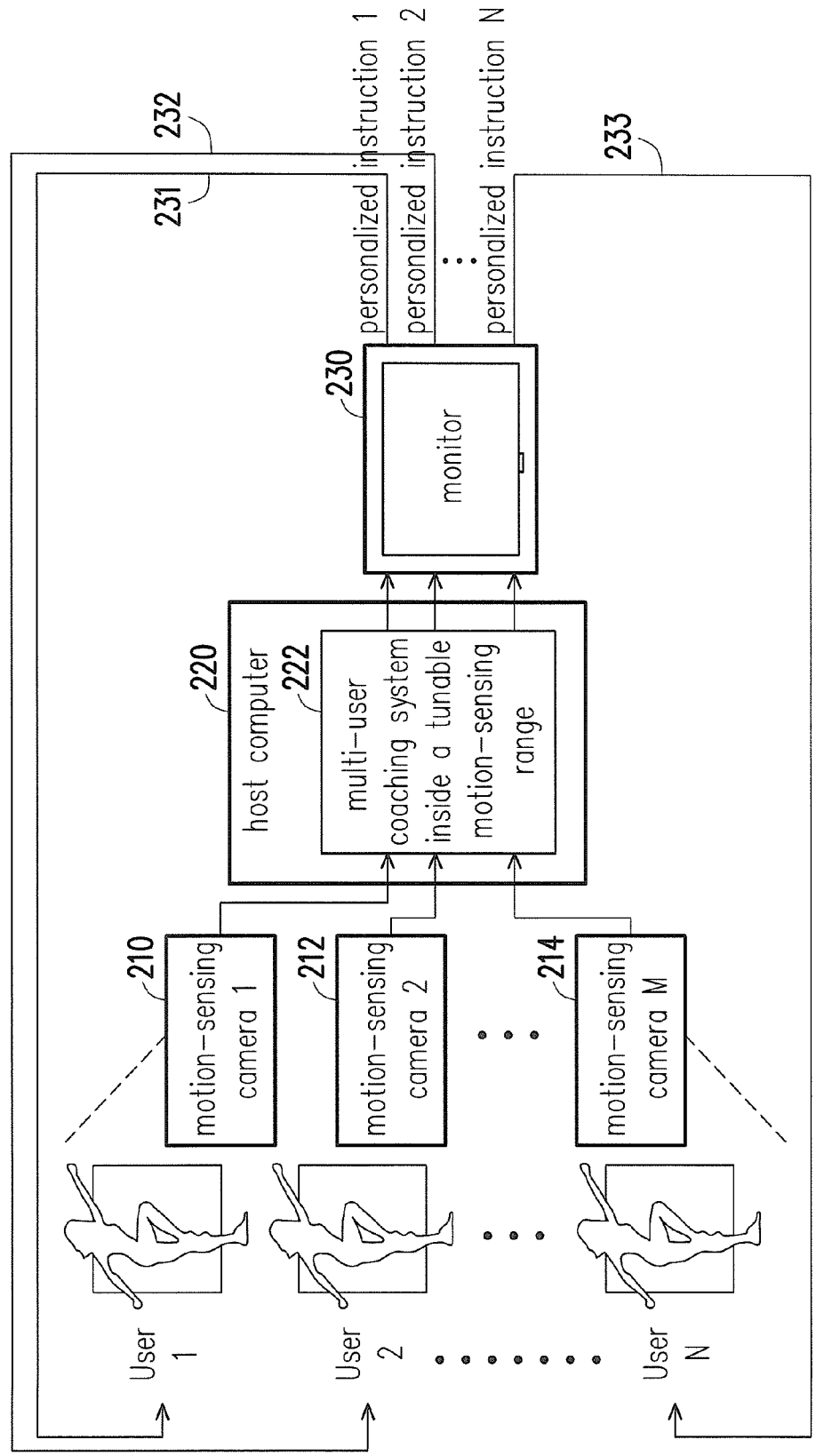
FIG. 2 is a schematic diagram illustrating setup environment of using the multi-user coaching system inside a tunable motion-sensing range according to the present exemplary embodiment.

Please refer to FIG. 2. FIG. 2 is a schematic diagram illustrating setup environment of using the multi-user coaching system inside a tunable motion-sensing range according to the present exemplary embodiment. There are N users (from user 1 to user N, as shown in FIG. 2) and plural sensors (e.g., M motion-sensing cameras as shown in FIG. 2), for example, the motion-sensing cameras 210-214. However, the disclosure is not limited thereto. The N users can follow the virtual coach in the monitor to move or do exercise in the setup environment that there are plural the motion-sensing cameras inside a tunable motion-sensing range.

The image data captured by the M motion-sensing cameras are transmitted to a host computer 220. A multi-user coaching system 222 inside a tunable motion-sensing range provided in the exemplary embodiment is configured in the host computer 220. The multi-user coaching system 222 can be executed due to the hardware architecture within the host computer 220 or any independent hardware architecture, which does not depart from the scope of the disclosure. According to the images captured by the motion-sensing cameras 210-214, a virtual environment of the multi-user coaching system 222 is established, and the information can be output and displayed to the monitor 230. Each user can be coached individually by a one-to-multiple approach to improve his or her motions at the same time. As shown in FIG. 2, the monitor 230 displays from the personalized instruction 1 to the personalized instruction N, (e.g., the personalized instructions 231-233) correspondingly provided to the N users, respectively.

During exercise, N users' depth streaming motion images and the skeleton node information can be captured at the same time from a new stitched depth image input by a user motion capturing unit. Additionally, the virtual coach motion information unit provides the recorded virtual coach depth streaming motion images and the skeleton node information. The multithreading processing unit processes the N users' skeleton inputted to one single calculation unit to process motion similarity comparisons in continuous time frames. The individual motion is compared and analyzed according to the motion trajectory of the visual coach and the motion trajectories of the N users in terms of the direction, the speed, and the distance. On the other hand, the multithreading processing unit also processes the depth images of N individual users inputted to the user gravity calculating unit, and the virtual coach motion information unit provides the depth image inputted to the virtual coach gravity calculating unit. Then the calculation unit compares the gravity shifting analyzing result at the same time; according to the personalized comparing results and the personalized gravity shifting comparing and analyzing results, a coaching database which stores the advices of the motion instructions is searched, and N appropriate personalized motion instructions are output to and displayed on a monitor for the users.

Figure 3:
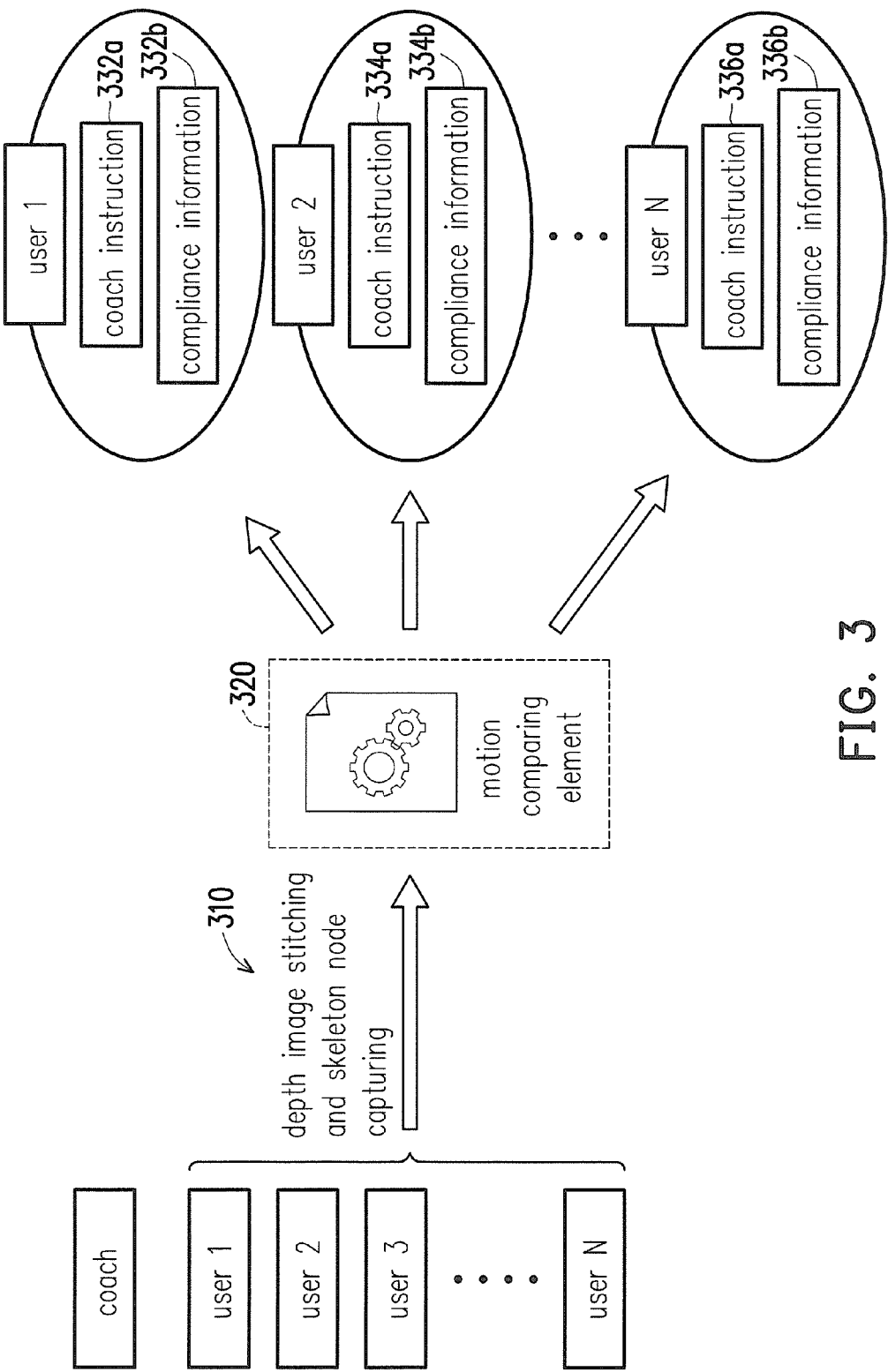
FIG. 3 is a schematic diagram illustrating the multi-user coaching system inside a tunable motion-sensing range according to the embodiment, and the multi-user coaching system inside a tunable motion-sensing range provides personalized instructions by a one-to-multiple approach.

Please refer to FIG. 3. FIG. 3 is a schematic diagram illustrating the multi-user coaching system inside a tunable motion-sensing range according to the embodiment, and the multi-user coaching system inside a tunable motion-sensing range provides the personalized motion instructions by a one-to-multiple approach. N users follow the coach to perform specific motions together. After the sensors obtain the images, the user information of the N users can be obtained, and the user information includes the users' depth image information and the skeleton node information (as shown in step 310). After comparison and calculation (as shown in step 320), the information of the personalized instructions is output. In one of several exemplary embodiments, the comparison and calculation includes the comparison between motions of multiple users and motions of the virtual coach as well as the comparison and analysis of the trajectories of the user depth streaming motion images and the corresponding virtual coach depth streaming motion trajectory. After comparison and calculation (as shown in step 320), the personalized instruction information for individual user is generated and displayed on the monitor. For example, the personalized instruction information provided to the user 1 includes the coach instruction 332a and the compliance information 332b, the personalized instruction information provided to the user 2 includes the coach instruction 334a and the compliance information 334b, and the personalized instruction information provided to the user N includes the coach instruction 336a and the compliance information 336b.

The comparison and calculation in one of several exemplary embodiments can refer to comparison of gravity. After the user information of N users is obtained, e.g., the depth image information and the skeleton node information, gravity comparison can be performed. First, the gravity of the depth streaming image of virtual coach is calculated, and the gravity of the depth streaming image of each individual user is calculated at the same time. The individual users' gravity shifting trajectories are analyzed and compared with the visual coach gravity shifting trajectory at the same time, and the corresponding personalized gravity shifting comparing and analyzing result is provided. In another embodiment, the motion and the gravity can be compared in parallel at the same time according to the obtained user information.

Figure 4:
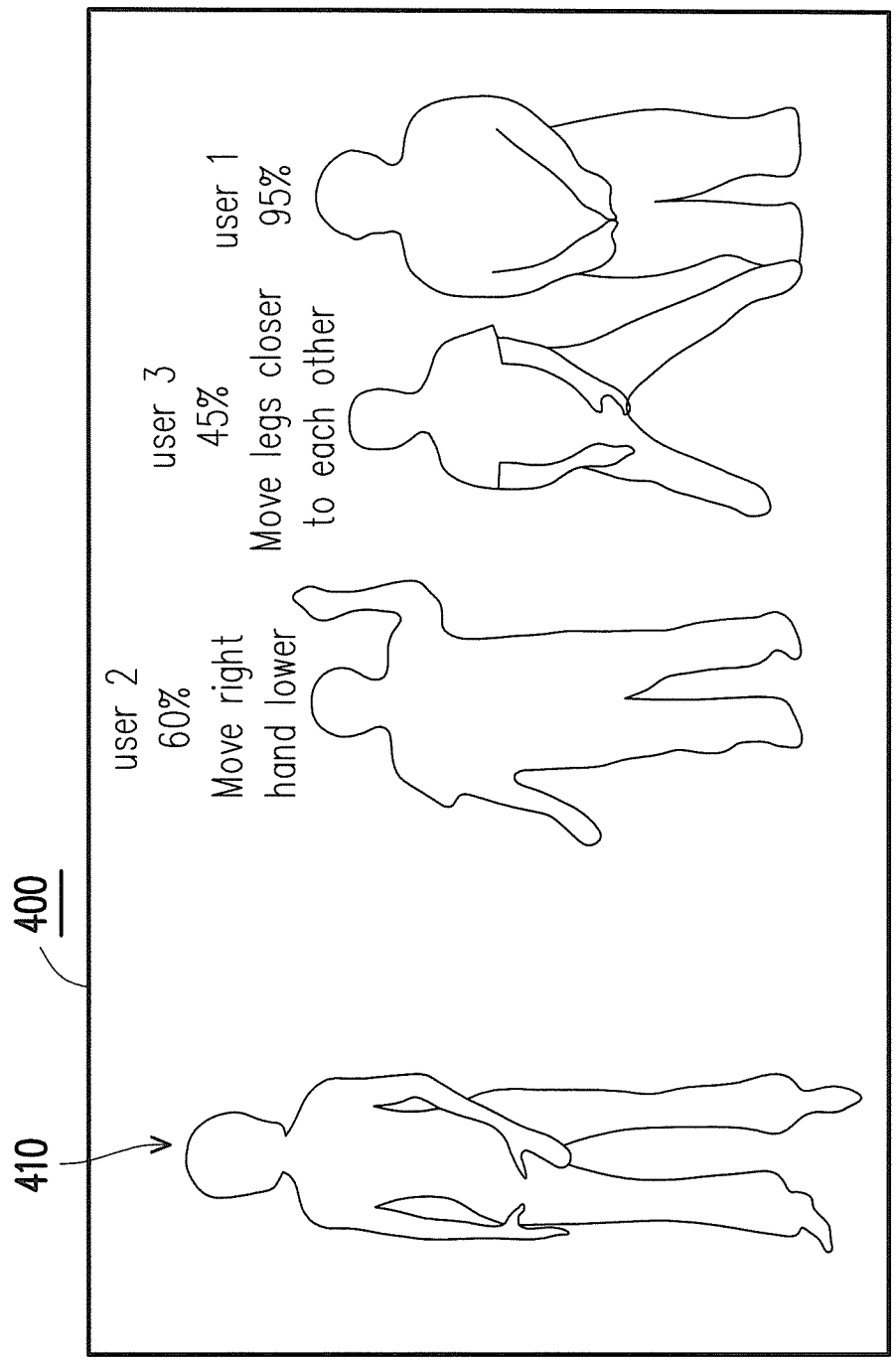
FIG. 4 is a schematic diagram illustrating virtual scenario of using the multi-user coaching system inside a tunable motion-sensing range to provide personalized instructions by a one-to-multiple approach.

Please refer to FIG. 4. FIG. 4 is a schematic diagram illustrating virtual scenario of using the multi-user coaching system inside a tunable motion-sensing range to provide personalized instructions by a one-to-multiple approach. Suppose that the virtual coach 410 in the virtual environment 400 displays a motion, and from the user 1 to the user 3 follow the virtual coach 410 to do a corresponding motion, respectively, the user information of these users can be obtained via the multi-user coaching system, e.g. the users' depth image information and the skeleton node information, etc. After comparison (e.g., the comparison between the trajectories of the user depth streaming motion images and the trajectory of the corresponding virtual coach depth streaming motion image or the comparison of the gravity), the personalized instruction information of each user is displayed on the monitor, respectively. For example, the comparing result of the user 1 is 95%; because the result meets the criteria, there is no need to provide further coaching instruction. The comparing result of the user 3 is 45%; because the result does not meet the criteria, the coaching instruction such as "move legs closer to each other" shown in the figure is further required. The comparing result of the user 2 is 60%; because the result does not meet the criteria, the coaching instruction such as "move right hand lower" shown in the figure is further required.

Then, components in the multi-user coaching system inside a tunable motion-sensing range are explained below.

Figure 5:
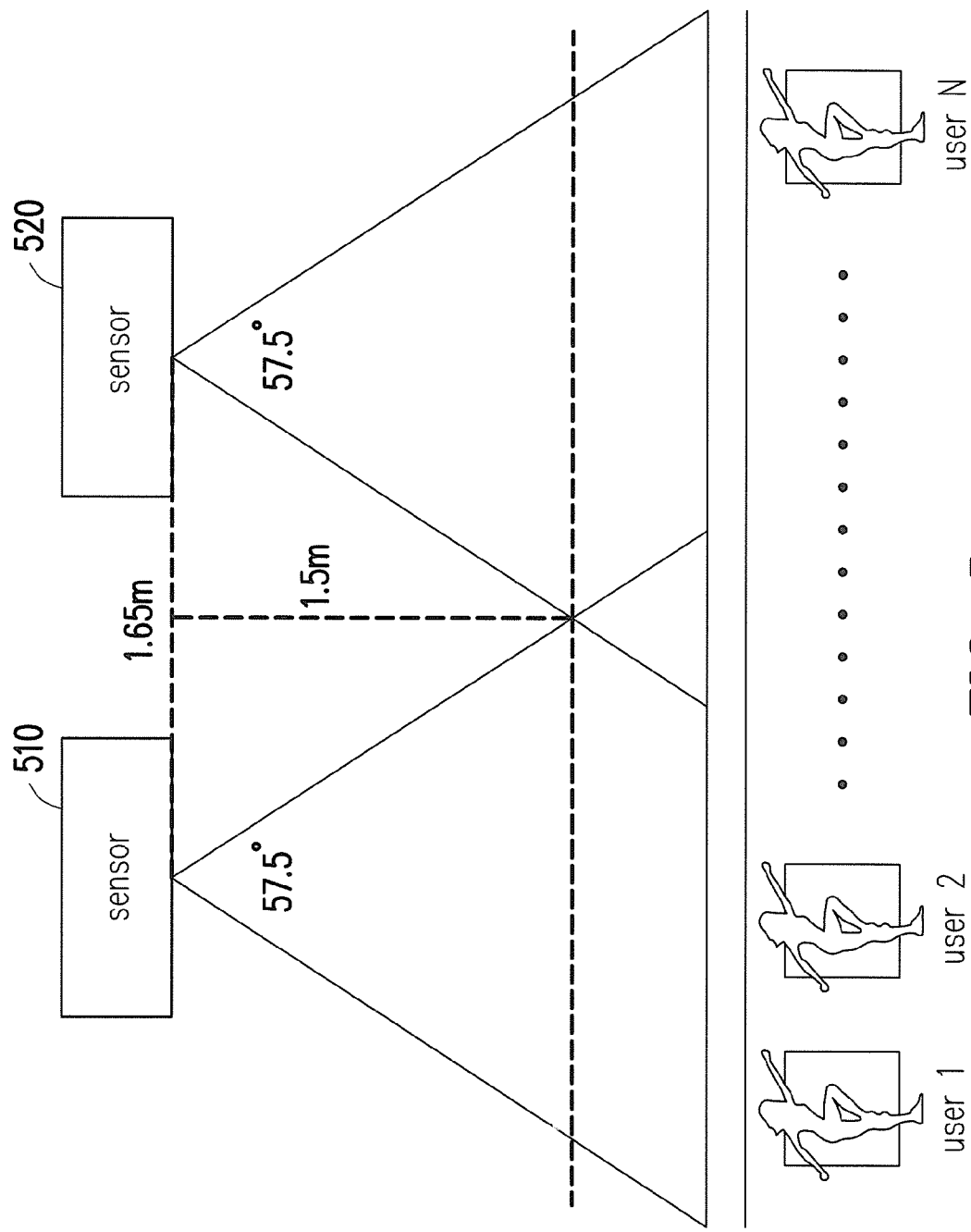
FIG. 5 is a schematic diagram illustrating the layout of a sensor set according to one of several exemplary embodiments of the disclosure.

Please refer to FIG. 5. FIG. 5 is a schematic diagram illustrating the layout of a sensor set according to one of several exemplary embodiments of the disclosure. The sensor set is used to detect and capture the images which at least include the images of multiple users, and the arrangement of the sensor set can be different in response to various environmental requirements. In the present exemplary embodiment, the sensor set is at a place where two motion-sensing cameras 510 and 520 are located. The sensing range of the known motion-sensing camera at the horizontal (x-axis) direction is 57.5°. According to specification requirements, the dual motion-sensing cameras should be placed at the same height (y-axis) in parallel, with the same view angle, and with the valid detection depth range (z-axis) behind 1.5 meter. Therefore, the distance between the dual motion-sensing cameras 510 and 520 should be at least 1.65 meter.

Figure 6:
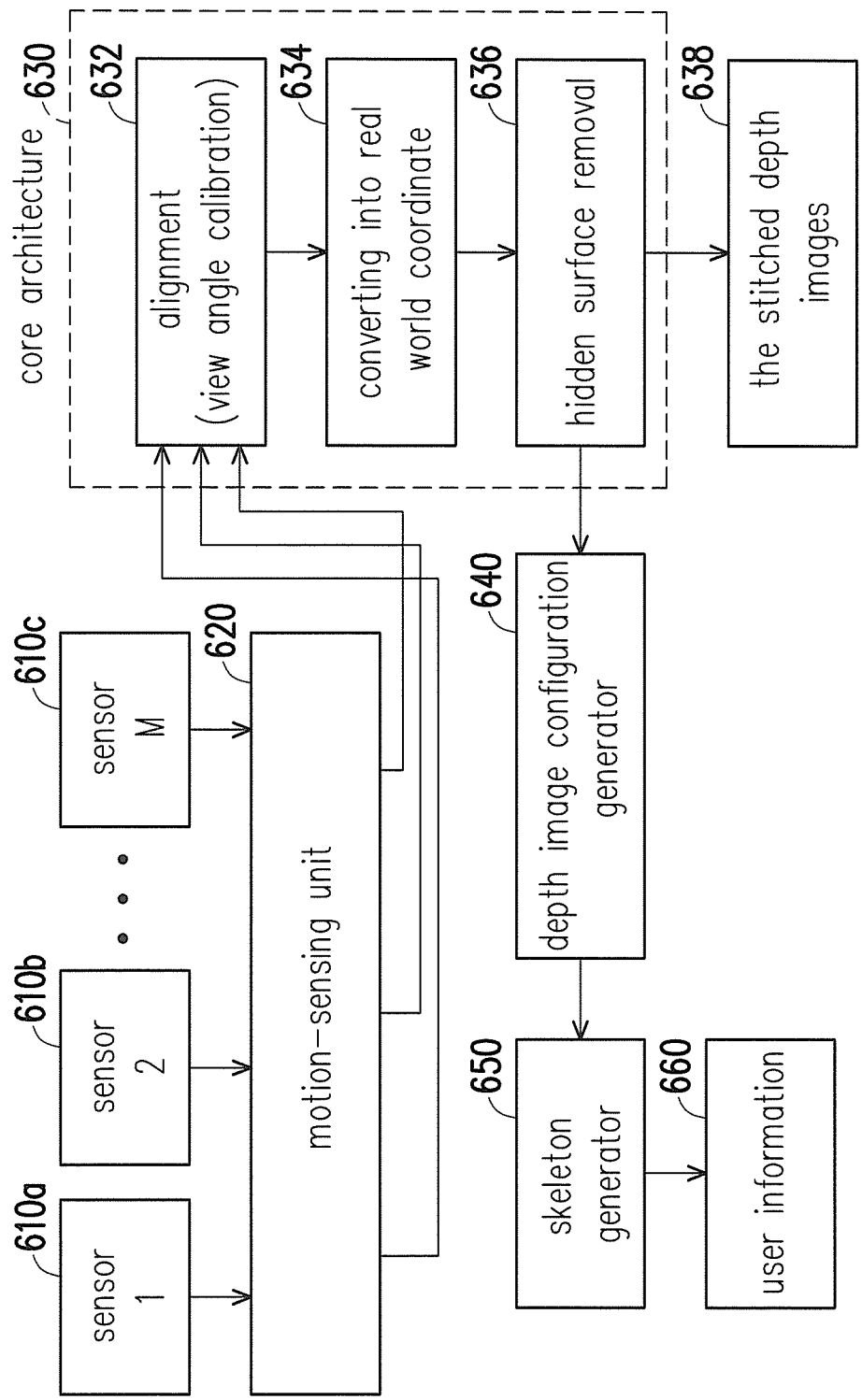
FIG. 6 is a schematic diagram of the architecture of a tunable depth image stitching unit and a user skeleton capturing unit according to one of several exemplary embodiments of the disclosure.

Please refer to FIG. 6. FIG. 6 is a schematic diagram of the architecture of a tunable depth image stitching unit and a user skeleton capturing unit according to one of several exemplary embodiments of the disclosure. After the motion-sensing unit 620 obtains the depth information from the motion-sensing cameras 610a, 610b, and 610c, the core architecture 630 performs signal processing in step 632. According to the previously assumed position of the motion-sensing cameras, plural sets of points corresponding to the real world coordinate can be obtained, and an alignment process is performed by a calibration function, e.g., the view angles of the motion-sensing cameras are calibrated. In step 634, the aligned information is projected to generate new depth information and converted into the real world coordinate. After the foregoing steps are completed, the hidden surface can be further removed in step 636. The new depth information is in form of meta data, and the data are transmitted to the skeleton generator 650 via the depth image configuration generator 640 to obtain the user information 660.

In one of several exemplary embodiments in this disclosure, the foregoing calibration function is a function of calibrating the view angles of the motion-sensing cameras and includes following step. First, a feature extraction method is performed to detect a plurality of feature points of RGB images in every two motion-sensing cameras, and the nearest neighbors search method is applied to obtain the correlations between feature points in every two of the RGB images. Since 1) the overlapping rate of every two images is not high because the depth values of the feature points for every dual image are too close, 2) the feature points on the left pixel of left image and the right pixel of right image in the horizontal (x-axis) direction is invalid due to the low overlapping rate, 3) the difference in every two feature points in dual RGB images in a vertical (y-axis) direction should not be significant, 4) the position distribution of every two corresponding feature points is unified, and 5) the depth values along with feature points are converted into the real word coordinates, by converting the depth values along with feature points to world coordinates, the x-axis difference in every two corresponding feature points can be obtained, the x-axis difference in every two corresponding feature points is sorted, and pairs of the corresponding feature points are obtained. These pairs of the corresponding points are characterized by the high correction rate. The foregoing process is stopped until the corresponding points with the obtained high correction rate, and whether the high correction rate can be determined by a threshold value.

Every two corresponding points obtained by performing said step can be divided into two groups. The first group is the feature points of image A, and the second group is the feature points of image B. With respect to the feature points of the first group as the basis, the feature points of the second group are rotated along with the horizontal (x-axis) and vertical (y-axis) directions, respectively. By calculating the angle of the nearest distance of the two groups of feature points in the real world coordinate, the view angle of image B can be calibrated, and the different diagrams illustrating can be completed by comparing before and after the calibrating view angles of every two images. After the calibration and the stitching steps are performed on every two of the images, the final depth images 638 are obtained. The final depth images 638 are, in form of meta data, transmitted via the depth image configuration generator 640 to the user skeleton generator 650, so as to obtain the user information and track the user skeleton. Therefore, the depth image and skeleton of the user can be tracked and captured from the final stitched depth image 638.

From the foregoing, the limitation of the horizontal view angle (57.5°) for one single motion-sensing camera no longer exits, and the motion-sensing range can be expanded and dynamically adjusted. As to the existing issue that the motion-sensing system is merely applicable to one single user, skeletons of multiple users are input to a motion similarity comparing element, and the motion similarity and the motion instructions of the individual user are calculated as shown in FIG. 3.

Figure 7:
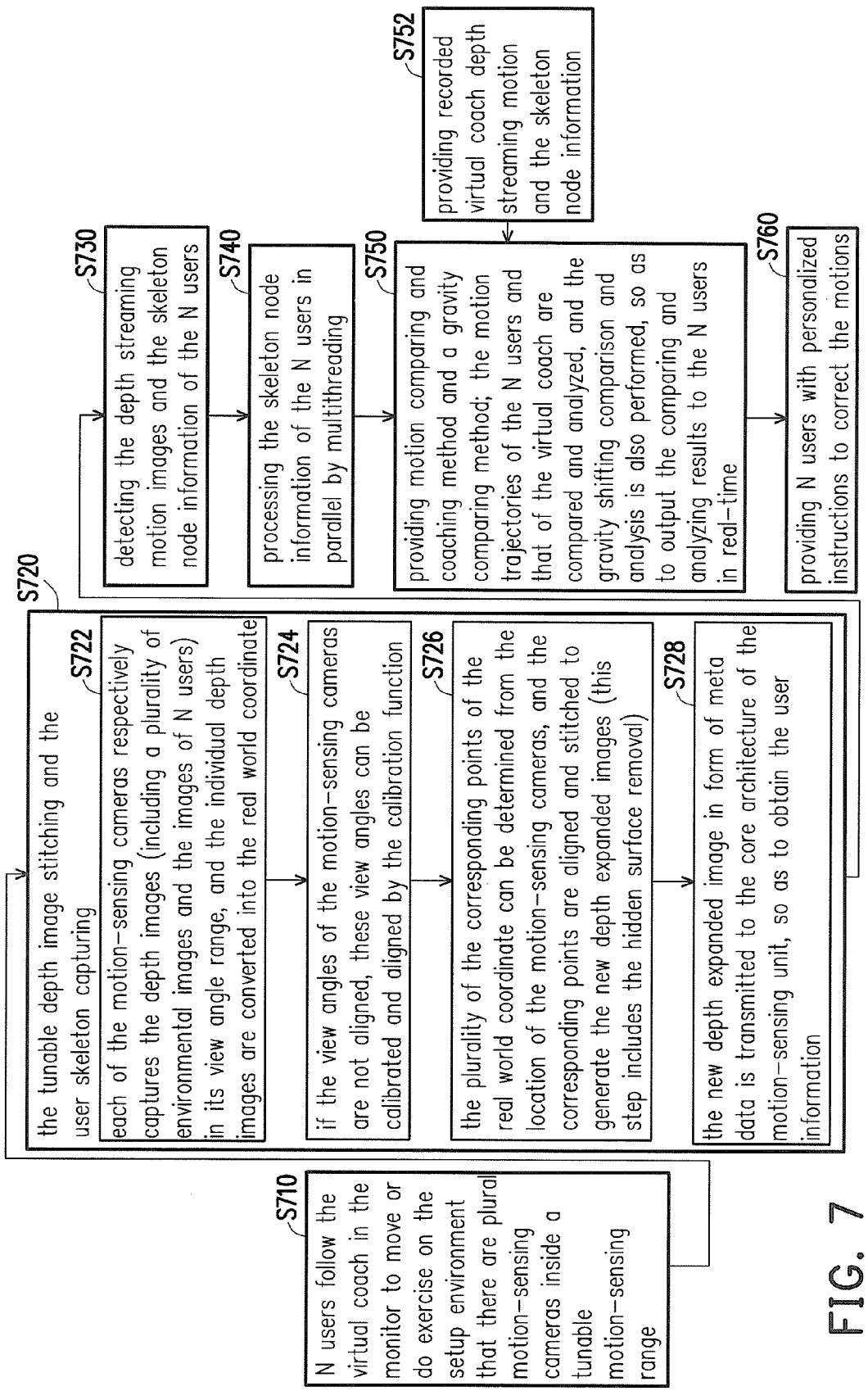
FIG. 7 is a flowchart illustrating a method applied to the multi-user coaching system inside a tunable motion-sensing range according to one of several exemplary embodiments of the disclosure.

Please refer to FIG. 7. FIG. 7 is a flowchart illustrating a method applied to the multi-user coaching system inside a tunable motion-sensing range according to one of several exemplary embodiments of the disclosure. First, in step S710, N users follow the virtual coach in the monitor to move or do exercise on the setup environment that there are plural motion-sensing cameras inside a tunable motion-sensing range. Step S720 includes steps S722 to S728 and shows a tunable depth image stitching process and a user skeleton capturing process.

In step S722, each of the motion-sensing cameras respectively captures the depth images (including a plurality of environmental images and the images of N users) in its view angle range, and the individual depth images are converted into the real world coordinate. In step S724, if the view angles of the motion-sensing cameras are not aligned, these view angles can be calibrated and aligned by the calibration function. In step S726, the plurality of the corresponding points of the real world coordinate can be determined from the location of the motion-sensing cameras, and the corresponding points are aligned and stitched to generate the new depth expanded images. Note that this step includes the hidden surface removal step. In step S728, the new depth expanded image in form of meta data is transmitted to the core architecture of the motion-sensing unit, so as to obtain the user information. In step S730, the depth streaming motion images and the skeleton node information of the N users are detected.

In step S740, the skeleton node information of the N users are processed in parallel by multithreading. In step S752, a recorded virtual coach depth streaming motion and the skeleton node information are provided. In step S750, a motion comparing and coaching method and a gravity comparing method are provided. The motion trajectories of the N users and that of the virtual coach are compared and analyzed, and the gravity shifting comparison and analysis is also performed. The comparing and analyzing results are output to the N users in real-time. In step S760, personalized instructions are provided to the N users to correct the motions.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A multi-user coaching system comprising:
    an image processing unit, receiving a plurality of images in parallel and performing a depth image stitching process and a user skeleton capturing process on the plurality of images to obtain a plurality of user information;
    a user motion capturing unit, generating a plurality of depth streaming motion images and a plurality of node information corresponding to each of the plurality of user information;

a multithreading processing unit, transmitting in parallel the node information and the plurality of depth streaming motion images corresponding to the plurality of user information;

a multi-user comparing unit coupled to the multithreading processing unit, wherein the multi-user comparing unit receives and compares the plurality of depth streaming motion images and the node information with virtual coach information to generate a plurality of personalized comparing results; and a coaching database, storing a plurality of predetermined motion instructions and outputting and displaying the motion instructions corresponding to the personalized comparing results.

2. The multi-user coaching system according to claim 1, wherein the multi-user comparing unit comprises a multi-user motion comparing unit coupled to the multithreading processing unit, the multi-user motion comparing unit receives the plurality of depth streaming motion images and the plurality of node information and compares motion trajectories of the plurality of depth streaming motion images with a plurality of virtual motion trajectories of the virtual coach information, and results of the comparison are configured as the personalized comparing results.

3. The multi-user coaching system according to claim 2, wherein the multi-user motion comparing unit comprises:

a virtual coach motion information unit, providing the plurality of virtual coach information which is pre-recorded; and a first calculation unit, coupled to the multithreading processing unit and the virtual coach motion information unit, wherein the first calculation unit simultaneously compares the motion trajectories of the plurality of depth streaming motion images and the virtual motion trajectories.

4. The multi-user coaching system according to claim 1, wherein the multi-user comparing unit comprises a multi-user gravity comparing unit coupled to the multithreading processing unit, the multi-user gravity comparing unit receives the plurality of depth streaming motion images and the plurality of node information, calculates gravity of the plurality of depth streaming motion images at the same time, and compares with a virtual coach gravity shifting trajectory, and results of the comparison are configured as the personalized comparing results.

5. The multi-user coaching system according to claim 4, wherein the multi-user gravity comparing unit comprises:

a virtual coach gravity calculating unit, obtaining the plurality of virtual coach information, calculating the gravity of virtual coach depth streaming images of the virtual coach information;

a user gravity calculating unit, coupled to the multithreading processing unit, the user gravity calculating unit receiving the plurality of depth streaming motion images and the plurality of node information and calculating the gravity of the plurality of depth streaming motion images ; and a second calculation unit, comparing the gravity of the plurality of depth streaming motion images and the gravity of the virtual coach depth streaming image, and providing corresponding personalized gravity shifting comparing results as the personalized comparing results.

6. The multi-user coaching system according to claim 1, further comprising a sensor set configured to sense and obtain the plurality of images and output the plurality of images to the image processing unit, wherein the sensor set comprises a plurality of sensors arranged according to an environmental requirement.

7. The multi-user coaching system according to claim 1, wherein the image processing unit comprises a tunable depth image stitching unit, and the tunable depth image stitching unit comprises:

a core architecture, receiving the images and performing an alignment process on the plurality of images by a calibration function to calibrate view angles of the plurality of images and convert the plurality of images to a real world coordinate; and a depth image configuration generator coupled to the core architecture, wherein the depth image configuration generator performs the depth image stitching process on the images converted into the real world coordinate to perform the depth image stitching on the plurality of images.

8. The multi-user coaching system according to claim 7, wherein the image processing unit comprises a user skeleton capturing unit coupled to the tunable depth image stitching unit to obtain the plurality of images after the depth image stitching process, and the user skeleton capturing process is performed on the plurality of images to obtain each of the node information of the user information.

9. A multi-user coaching method, comprising:

receiving a plurality of images in parallel and performing a depth image stitching process and a user skeleton capturing process on the plurality of images to obtain a plurality of user information;

generating a plurality of depth streaming motion images and a plurality of node information corresponding to each of the user information;

comparing the plurality of depth streaming motion images and each of the plurality of node information with virtual coach information to generate a plurality of personalized comparing results; and outputting and displaying a plurality of motion instructions corresponding to the personalized comparing results.

10. The method according to claim 9, wherein the step of comparing the plurality of depth streaming motion images and each of the plurality of node information with the virtual coach information comprises:

comparing motion trajectories of the plurality of depth streaming motion images with a plurality of virtual motion trajectories of the virtual coach information wherein results of the comparison are configured as the personalized comparing results.

11. The method according to claim 10, wherein the step of comparing the motion trajectories of the plurality of depth streaming motion images with the plurality of virtual motion trajectories of the virtual coach information comprises:

providing the plurality of virtual coach information which is pre-recorded; and comparing the motion trajectories of the plurality of depth streaming motion images with the plurality of virtual motion trajectories of the virtual coach information at the same time.

12. The method according to claim 9, wherein the step of comparing the plurality of depth streaming motion images and the node information with the virtual coach information comprises:

calculating gravity of the plurality of depth streaming motion images and comparing with a plurality of virtual coach gravity shifting trajectories, wherein results of the comparison are configured as the personalized comparing results.

13. The method according to claim 12, wherein the step of calculating the gravity of the plurality of depth streaming motion images and comparing with the plurality of virtual coach gravity shifting trajectories comprises:
   obtaining the virtual coach information and calculating the gravity of a virtual coach depth streaming image of the virtual coach information;
   calculating the gravity of the plurality of depth streaming motion images at the same time; and
   comparing each of the gravity of the plurality of depth streaming motion images with the gravity of the virtual coach depth streaming image at the same time and providing corresponding personalized gravity shifting comparing results as the personalized comparing results.

14. The method according to claim 9, wherein the step of receiving the plurality of images in parallel, performing the depth image stitching process and the user skeleton capturing process on the plurality of images comprises:
   receiving the plurality of images and performing an alignment process on the plurality of images by a calibration function to calibrate view angles of the plurality of images and convert the plurality of images to a real world coordinate; and
   performing the depth image stitching process on the plurality of images converted into the real world coordinate to perform the depth image stitching on the plurality of images.

15. The method according to claim 14, wherein the step of performing the alignment process on the plurality of images by the calibration function comprises:
   detecting a plurality of feature points of every two of the plurality of images through performing a feature extraction process and obtaining plurality of feature correlations between the plurality of feature points of every two of the plurality of images through performing a nearest neighbors search process; and
   obtaining a determination value by performing calculations on the plurality of feature values, if the determination value is higher than a threshold, performing the alignment process according to the feature values.

16. The method according to claim 15, wherein in the step of obtaining the determination value by performing the calculations on the feature values, the determination value is adjusted if the depth values of the feature points are so close that an overlapping rate of the feature points of every two of the images is lower than a predetermined value.

17. The method according to claim 15, wherein the step of obtaining the determination value by performing the calculations on the feature values comprises
   converting the depth values along with the feature points into real world coordinates,
   obtaining a horizontal axis difference value of every two corresponding points,
   sorting the horizontal axis difference value of every two corresponding points, and
   picking out the corresponding points in pairs, wherein the picked out points are configured as the increasing determination value.

18. The method according to claim 14, wherein the step of receiving the images in parallel and performing the depth image stitching process and the user skeleton capturing process on the images further comprises
   performing the user skeleton capturing process on the plurality of images undergoing the depth image stitching process to obtain the node information of the user information.

\* \* \* \* \*